United States Patent
Hajianpour

(10) Patent No.: US 12,241,736 B1
(45) Date of Patent: Mar. 4, 2025

(54) APPARATUS FOR MEASURING THE HEIGHT OF A CHILD

(71) Applicant: Zoya Hajianpour, Fort Lauderdale, FL (US)

(72) Inventor: Zoya Hajianpour, Fort Lauderdale, FL (US)

( * ) Notice: Subject to any disclaimer, the term of this patent is extended or adjusted under 35 U.S.C. 154(b) by 449 days.

(21) Appl. No.: 17/860,012

(22) Filed: Jul. 7, 2022

Related U.S. Application Data

(63) Continuation-in-part of application No. 16/504,289, filed on Jul. 7, 2019, now Pat. No. 11,382,532.

(51) Int. Cl.
A61B 5/107 (2006.01)
G01B 3/20 (2006.01)
G01B 5/02 (2006.01)

(52) U.S. Cl.
CPC .............. *G01B 3/20* (2013.01); *A61B 5/1072* (2013.01); *G01B 5/02* (2013.01); *A61B 2503/06* (2013.01)

(58) Field of Classification Search
CPC .................................................. A61B 5/1072
USPC .......................................................... 33/512
See application file for complete search history.

(56) References Cited

U.S. PATENT DOCUMENTS

| | | | | |
|---|---|---|---|---|
| 1,974,085 A * | 9/1934 | Shields | ................... | G01B 5/061 33/512 |
| 1,985,527 A * | 12/1934 | Taylor | .................... | G01G 19/50 33/512 |
| 2,215,884 A * | 9/1940 | Runge | ...................... | G01B 5/02 126/30 |
| 2,381,428 A * | 8/1945 | Attick | .................. | A61B 5/1072 33/720 |
| 4,939,849 A * | 7/1990 | Johnson | ................... | G01B 5/02 33/712 |
| 6,237,239 B1 * | 5/2001 | Miyazaki | ............. | A61B 5/1072 33/757 |
| 8,109,008 B1 * | 2/2012 | Niemczak | ............ | A61B 5/1079 600/587 |
| 8,528,221 B2 * | 9/2013 | Glock, Jr. | ............ | A61B 5/1072 600/587 |
| 8,539,690 B2 * | 9/2013 | Haykeen | .............. | A61B 5/1072 600/587 |
| 8,845,332 B1 * | 9/2014 | Reid | .................... | A61B 5/1072 702/173 |
| 8,869,415 B1 * | 10/2014 | Haykeen | .............. | A61B 5/1072 33/485 |

(Continued)

*Primary Examiner* — George B Bennett
(74) *Attorney, Agent, or Firm* — Mark D. Bowen, Esq.; Malin Haley DiMaggio & Bowen, P.A.

(57) ABSTRACT

A device for measuring the height of a child, standing on a floor, near a wall, comprising a housing having a plastic molded front panel that includes a track member, and a molded pack panel attacked to the backside of said front panel; said housing attached to a wall. The housing front panel has a central space and a mirror to keep the attention of the child during the measuring process, and a visible scale and a carriage, each attached to the track member, with the carriage being vertically movable along the track member. The carriage can be manually moved by a user to correspond to the top level of the child's head, an indicator on the carriage points to a location on the visible scale indicating the height of the child. The front panel has a flat vertical surface parallel and next to the vertical track for a user to place indicia with a marker next to the carriage with child height measurement information.

3 Claims, 14 Drawing Sheets

(56) References Cited

U.S. PATENT DOCUMENTS

| | | | |
|---|---|---|---|
| 10,788,305 B1* | 9/2020 | Neu | G01B 3/1048 |
| 10,895,453 B2* | 1/2021 | Stemkens | G01B 13/20 |
| 11,172,847 B2* | 11/2021 | Johnston | G01B 11/0608 |
| 11,771,342 B2* | 10/2023 | Malcolm | A61B 5/1072 |
| | | | 33/512 |
| 2006/0288599 A1* | 12/2006 | Hajianpour | G01B 3/10 |
| | | | 33/755 |
| 2014/0109425 A1* | 4/2014 | Brotman | G01B 3/10 |
| | | | 33/759 |
| 2014/0202017 A1* | 7/2014 | Wood | G01B 3/20 |
| | | | 33/512 |
| 2021/0244315 A1* | 8/2021 | Malcolm | G01C 5/00 |

* cited by examiner

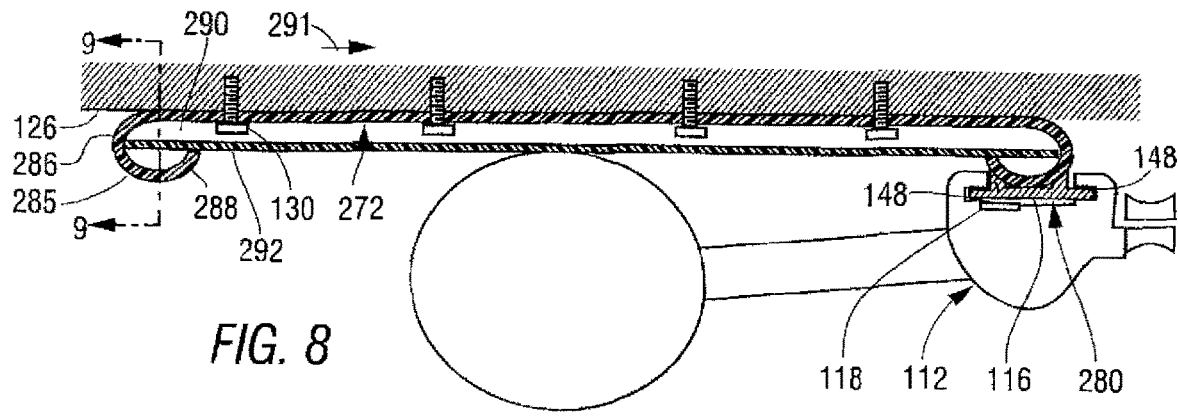
FIG. 8
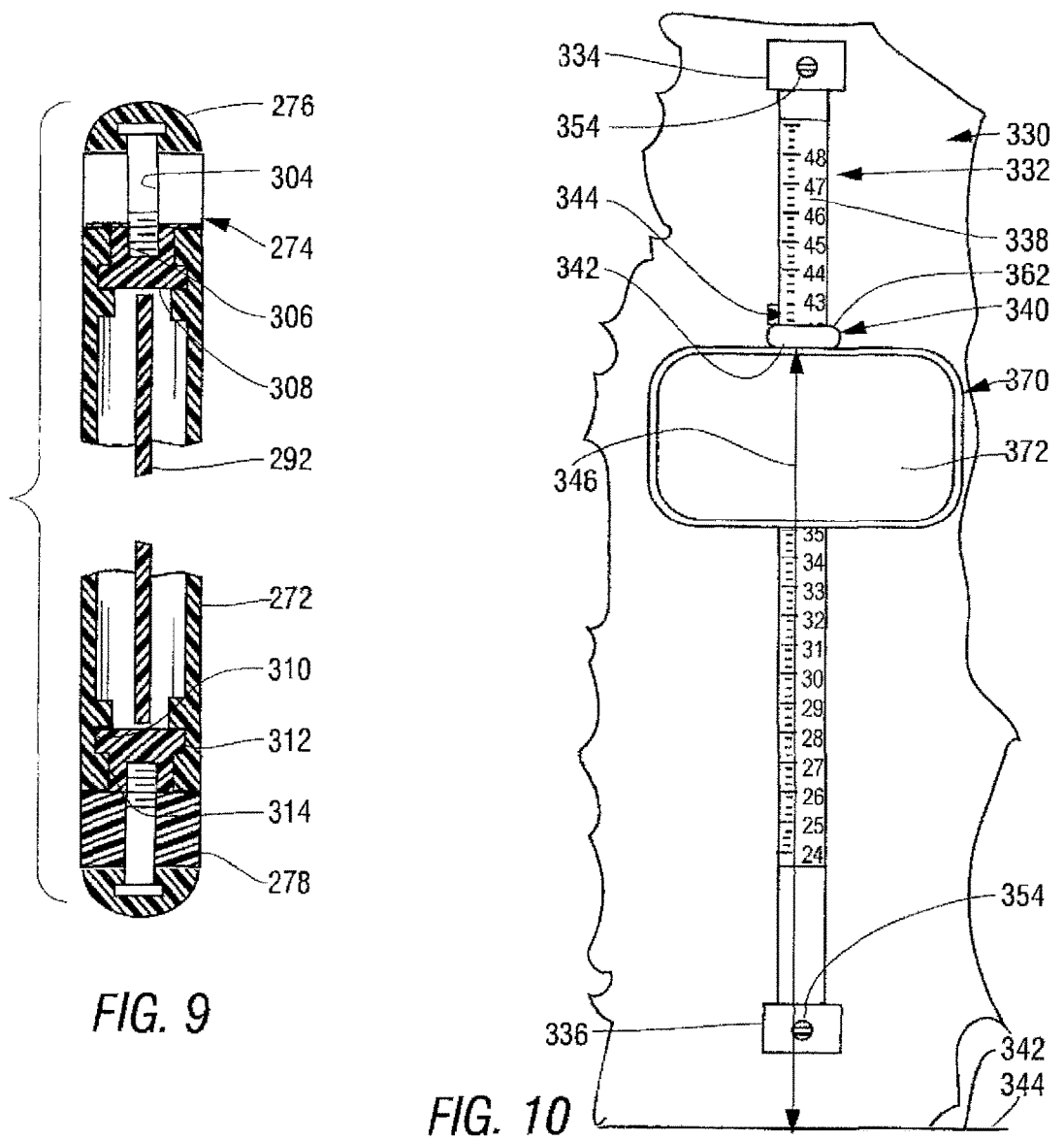
FIG. 9
FIG. 10

APPARATUS FOR MEASURING THE HEIGHT OF A CHILD

RELATED APPLICATIONS

This application is a continuation-in-part of U.S. Ser. No. 16/504,289 filed Jul. 7, 2019 Entitled: "Apparatus For Measuring The Height Of A Child".

FEDERALLY SPONSORED RESEARCH OR DEVELOPMENT

Not applicable

BACKGROUND OF THE INVENTION

Field of the Invention

This invention relates to an apparatus and a method for measuring the height of a child, and, more particularly, to such an apparatus including a device for maintaining the attention of the child during the measurement process.

Description of Related Art

While devices for measuring the height of babies, toddlers, and adults are well known, it is additionally known that it is often difficult to keep a baby or child still enough for the measurement process to be completed with conventional measuring apparatus. It is further known that babies, being fascinated when they see themselves in a mirror, often pause when they are presented with a mirror. The method of providing a mirror in a place where people have to wait works with adults, too, and has been used by hotels providing large mirrors adjacent elevator doors to avoid the alternative expense of providing additional elevators to reduce wait times.

While many individuals note their child's growth progress with a series of markings on a wall, and while a number of colorful posters are available for receiving such markings after being attached to a wall, what is needed is an apparatus for easily determining a child's growth progress in terms of measured units, such as inches or centimeters, for comparison with various forms of standard growth data.

SUMMARY OF THE INVENTION

Alternate Embodiments of the Invention

In accordance with an aspect of the invention, in an alternate embodiment, an apparatus is provided for measuring a height of a child standing at a predetermined location. The apparatus includes a track member, in some embodiments, attached to a wall, a visible scale attached to the track member, a measurement carriage attached to the track member, to be movable manually along the track member only vertically, a friction member formed as part of the carriage at its ends such that the carriage is held in contact with the track member, to stop and prevent motion of the carriage along the track member, and a mirror attached to the apparatus adjacent and parallel to one side of the track member, to be visible to the child standing in the preferred location for height measurement.

In some embodiments, the carriage includes a downward-facing measurement surface and an indicator moving adjacently along the visible scale, pointing to a place on the visible scale describing a vertical distance between the downward-facing measurement surface and the predetermined location.

In one alternate embodiment of the invention, the apparatus additionally includes a frame member extending along a distal side of the mirror, with the track member extending along a proximal side of the mirror, and with the mirror being attached to extend between the track member and the frame member. This version of the apparatus additionally includes an upper end cap attached to the wall, having sockets holding upper ends of the track member and the frame member, and a lower end cap attached to the wall, having sockets holding lower ends of the track member and the frame member, so that the track member is attached to the wall by the upper and lower end caps. Furthermore, in this version of the apparatus, the track member may include a slot holding a proximal edge of the mirror, while the frame member includes a slot holding a distal edge of the mirror, while the upper end cap includes a slot holding an upper edge of the mirror, and while the lower end cap includes a slot holding a lower edge of the mirror.

In another alternate embodiment of the invention, the apparatus additionally includes a main plate extending in a distal direction from the track member. The main plate includes a curved proximal flange forming a slot holding a proximal edge of the mirror and a distal flange curved to form a slot holding a distal edge of the mirror. The track member is attached to the proximal flange, and the main plate is attached to the wall, so that the track member is attached to the wall by the main plate. The apparatus further includes upper and lower end caps holding the mirror to extend between the slot in the proximal flange and the slot in the distal flange by closing openings within the main plate above and below the mirror. The apparatus may additionally include a first pair of attachment screws, each extending through a clearance hole in the upper cap and through a clearance hole in an upper strip of the main plate to engage a threaded hole in a clamping block held within a slot in the main plate and to clamp the upper strip of the main plate between the clamping block and the upper cap, and a second pair of attachment screws, each extending through a clearance hole in the lower cap and through a through a clearance hole in a lower strip of the main plate to engage a threaded hole in a clamping block held within a slot in the main plate and to clamp the lower strip of the main plate between the clamping block and the lower cap.

In yet another embodiment of the invention, the apparatus additionally comprises a mirror holding member, attached to the carriage and moving with the carriage, holding the mirror. This version of the apparatus additionally includes an upper end cap attached to the wall, having a socket holding an upper end of the track member, and a lower end cap attached to the wall, having a socket holding lower end of the track member, whereby the track member is attached to the wall by the upper and lower end cap.

For example, in some alternate embodiments, a brake member comprises a brake lever, pivotally mounted within the carriage, held in contact with the track member by a spring member, while the brake releasing member comprises a knob, that slides and is mounted within the carriage to move horizontally in and opposite a brake releasing direction, wherein movement of the knob in the brake releasing direction moves the brake lever away from the track member, and wherein movement of the knob in a vertical direction, with the brake lever held away from the track member, causes movement of the carriage in the vertical direction along the track member. Alternatively, the brake releasing member comprises a knob, slidable and mounted within the carriage to move horizontally in and opposite a brake releasing direction, wherein movement of the knob in the brake releasing direction moves the brake lever away from the track member, and wherein movement of the knob in a vertical direction with the brake lever held away from the track member causes movement of the carriage in the vertical direction along the track member.

In accordance with another aspect of the invention, a kit is provided, including the apparatus as described above for measuring a height of a child standing in a preferred location. The kit may additionally include an assembly fixture locating the lower end cap or the main plate on a wall so that the lower end of the track member placed within the lower end cap will be spaced away from the floor surface by the predetermined distance. In accordance with yet another aspect of the invention, a method is provided for installing a first apparatus for measuring a height of a child standing in a predetermined location. The method includes attaching a lower end cap to a wall at a predetermined distance from a floor surface extending outward from the wall, installing a second apparatus including a track member, a visible scale attached to the track member, a mirror facing the predetermined location, and a carriage attached to the track member to be movable along the track member only vellically, including a downward-facing measurement surface and an indicator moving adjacently along the visible scale, wherein the indicator points to a place on the visible scale describing a vertical distance between the downward-facing measurement surface and the floor surface to extend upward along the wall from a socket within the lower end cap; and attaching an upper end cap to the wall to hold an upper end of the second apparatus. The second additional side comprises a frame member extending along a distal side of the mirror, wherein the track member extends along a proximal side of the mirror, and wherein the mirror is attached to extend between the track member and the frame member, or alternately the second apparatus may include a mirror holding member, attached to the carriage and moving with the carriage, holding the mirror.

Summary of the Preferred Embodiment Invention

In the preferred embodiment of the invention disclosed herein, the invention is an apparatus or device comprising a rectangular housing, having a central, front rectangular mirror, mountable on a wall. The apparatus is constructed of a rectangular, plastic molded, front panel that secures the mirror, and a plastic molded back panel, the front and back panels fastened together by screws, firmly engaging the mirror in the child height measure housing.

The rectangular, molded front panel includes a vertical track member, preferably on the right side of the front panel, the vertical track member being engaged by a manually movable measurement carriage, semi-circular with bulbous free ends that grip small slots along the base on each side of the vertical track. The carriage mid-section has a child's height measurement scale viewing window, the carriage being manually moved against its two bulbous ends' friction with the front panel, movable vertically by a user. The vertical track member includes a numerical measuring scale, from top to bottom, with measurement lines and numerals, to indicate the height of the child, in either inches or centimeters. The carriage includes a front window viewing area that shows a few numerals of the scale measurement indicia, such as in inches or centimeters, in segments indicated by parallel horizontal lines, transcribed on the front frame panel vertical track surface to be visible in the carriage window area. The carriage has a middle, pointed arrowhead, facing into the window horizontally, at the height values measurement lines.

The entire device is hung on a wall surface by, preferably, six wall mounted bolts or screws that have round heads, that fit into the device molded, back panel slots, each slot receiving a bolt or screw head for support on a wall. The height of the device, and especially the vertical track measuring scale of measurement numbers, is positioned above the floor to accurately be the correct height of a child standing on the floor in front of the measuring device.

Extending horizontally outwardly from one side of the front panel adjacent the vertical track, on the right vertical side of the front panel is a flat, rectangular vertical surface, in the plane of the mirror, that can be used by some one measuring a child, to write with a marker pen on the panel surface, parallel to the carriage arrow, desired measurement information to show a height line, date and/or child information along the right vertical side of the device, in the preferred embodiment. The preferred embodiment is shown in FIGS. 14-23.

To measure the height of a child, looking at the preferred embodiment of the invention, described herein, a child will stand in front of the mirror located in the center of the measuring device, looking at the mirror mounted in the center of the apparatus frame. An adult can manipulate manually the carriage on the vertical track manually, against friction, directly over the measurement indicia transcribed on the vertical frame track, until the carriage points horizontally at the approximate level of the child's top of his head. And then, with a marker, the adult can place a horizontal mark on the right flat, vertical extending panel surface, and can provide any additional information concerning the child's age, name, or the like.

Various embodiments of the invention are shown in the drawings enclosed, including the preferred embodiment disclosed herein.

BRIEF DESCRIPTION OF THE DRAWINGS

These and other aspects of the invention will be made apparent by reading the following specification in conjunction with the accompanying figures, in which:

Alternate Embodiments of the Invention

FIG. 8 is a cross-sectional plan view of the apparatus of FIG. 7, taken as indicated by section line 8-8 therein;

FIG. 9 is a fragmentary cross-sectional elevation of the apparatus of FIG. 7, taken as indicated by section line 9-9 in FIG. 8;

FIG. 10 is a front elevation of an apparatus for measuring a height of a child, built in accordance with a third embodiment of the invention;

Preferred Embodiment the Invention

Figure 1:
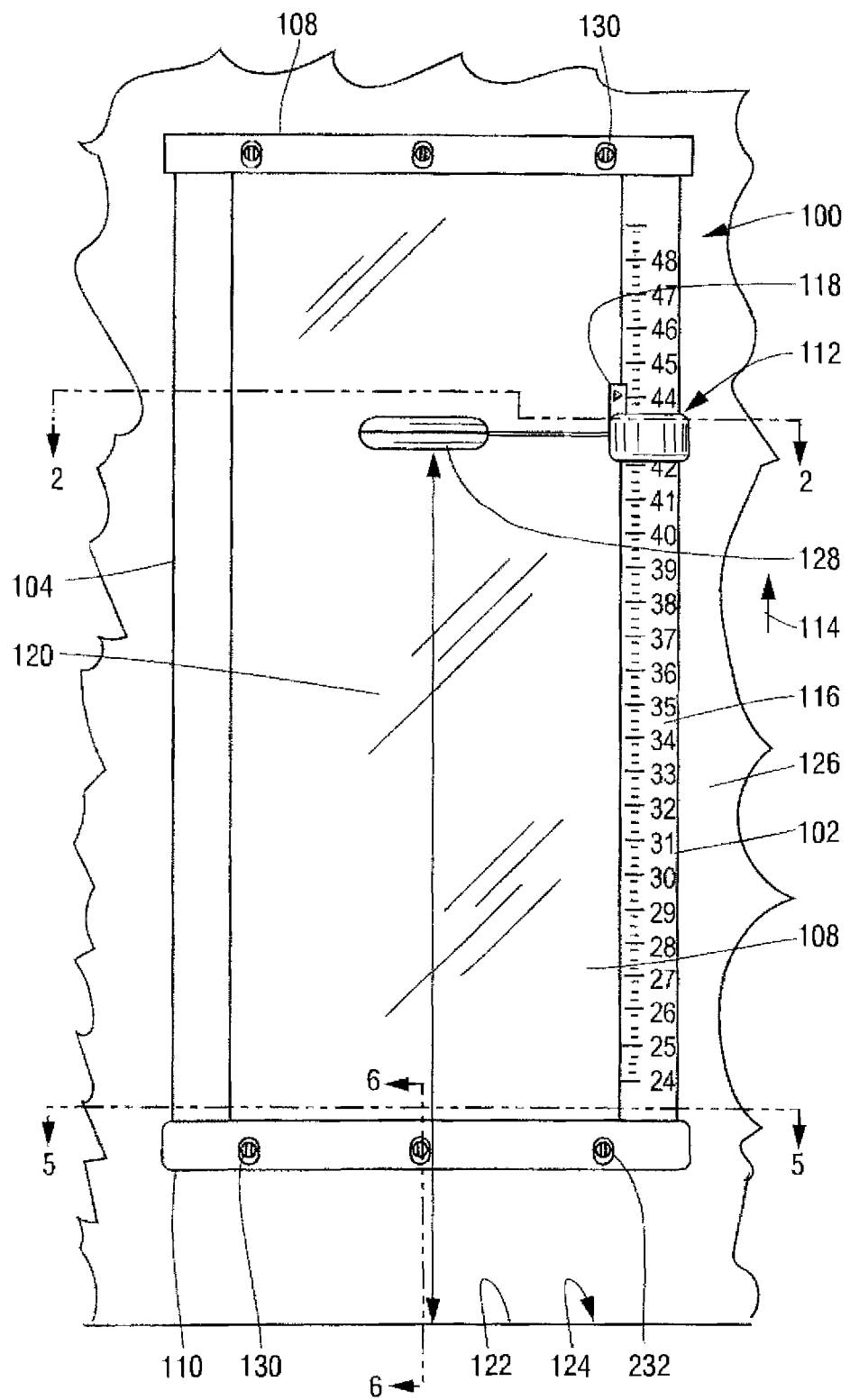
FIG. 1 is a front elevation of apparatus for measuring a height of a child, built in accordance with a first alternate embodiment of the invention.
Figure 7:
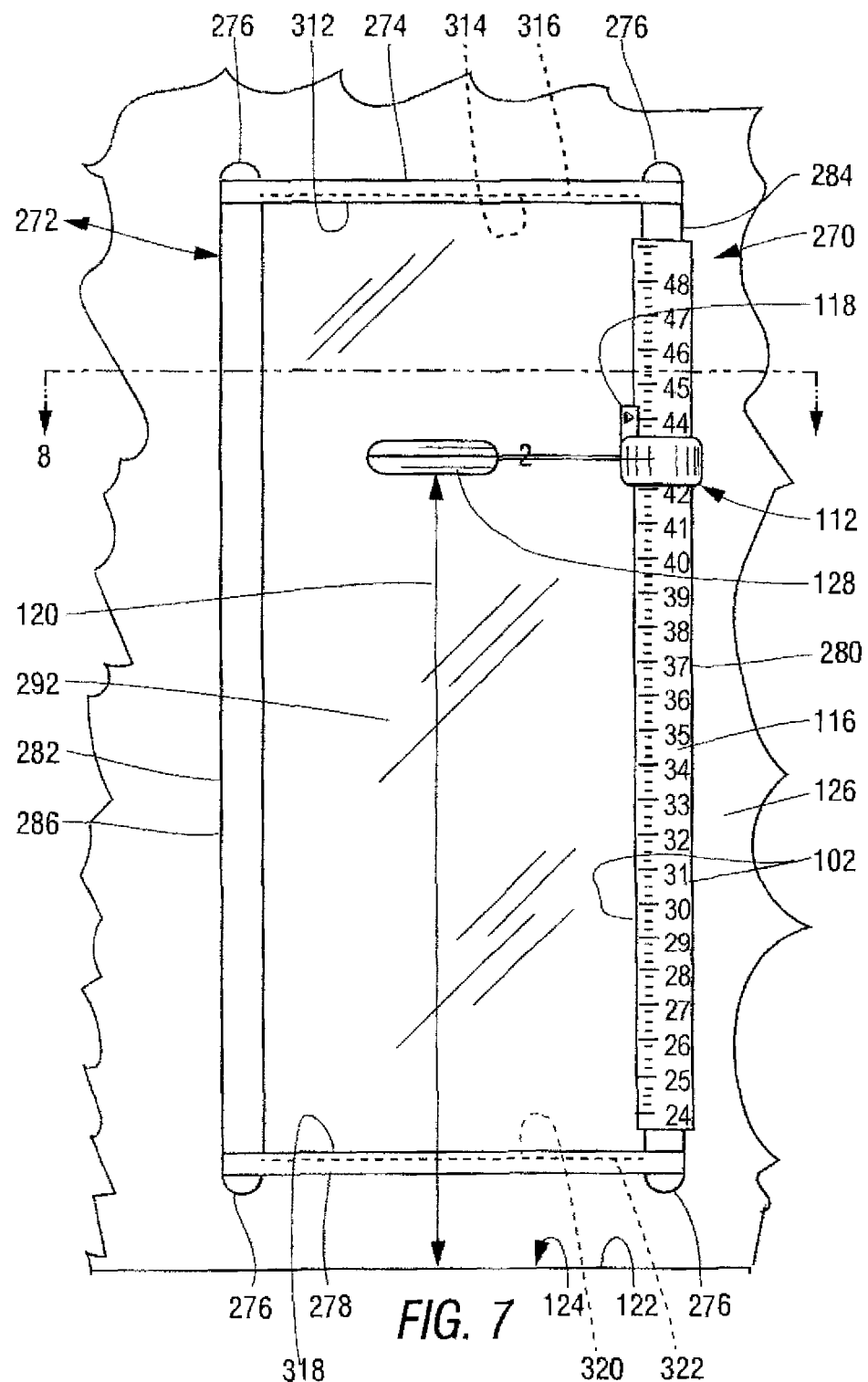
FIG. 7 is a front elevation of an apparatus for measuring a height of a child, built in accordance with a second embodiment of the invention.
Figure 13:
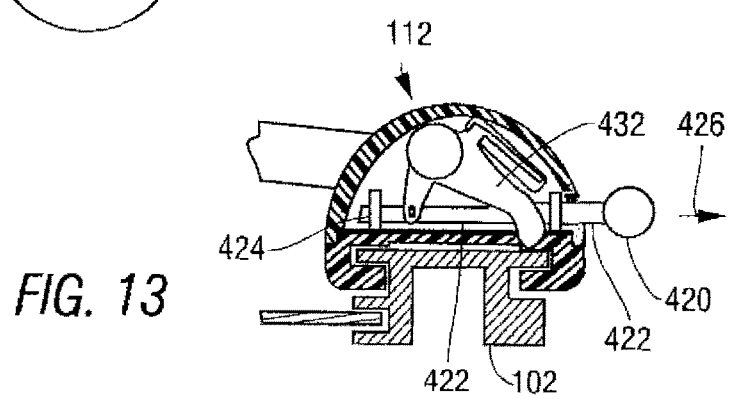

FIG. 13 is a plan view of a carriage within the apparatus of FIG. 1 or of FIG. 7, shown as configured in accordance with the alternative embodiments of the invention.

Figure 14:
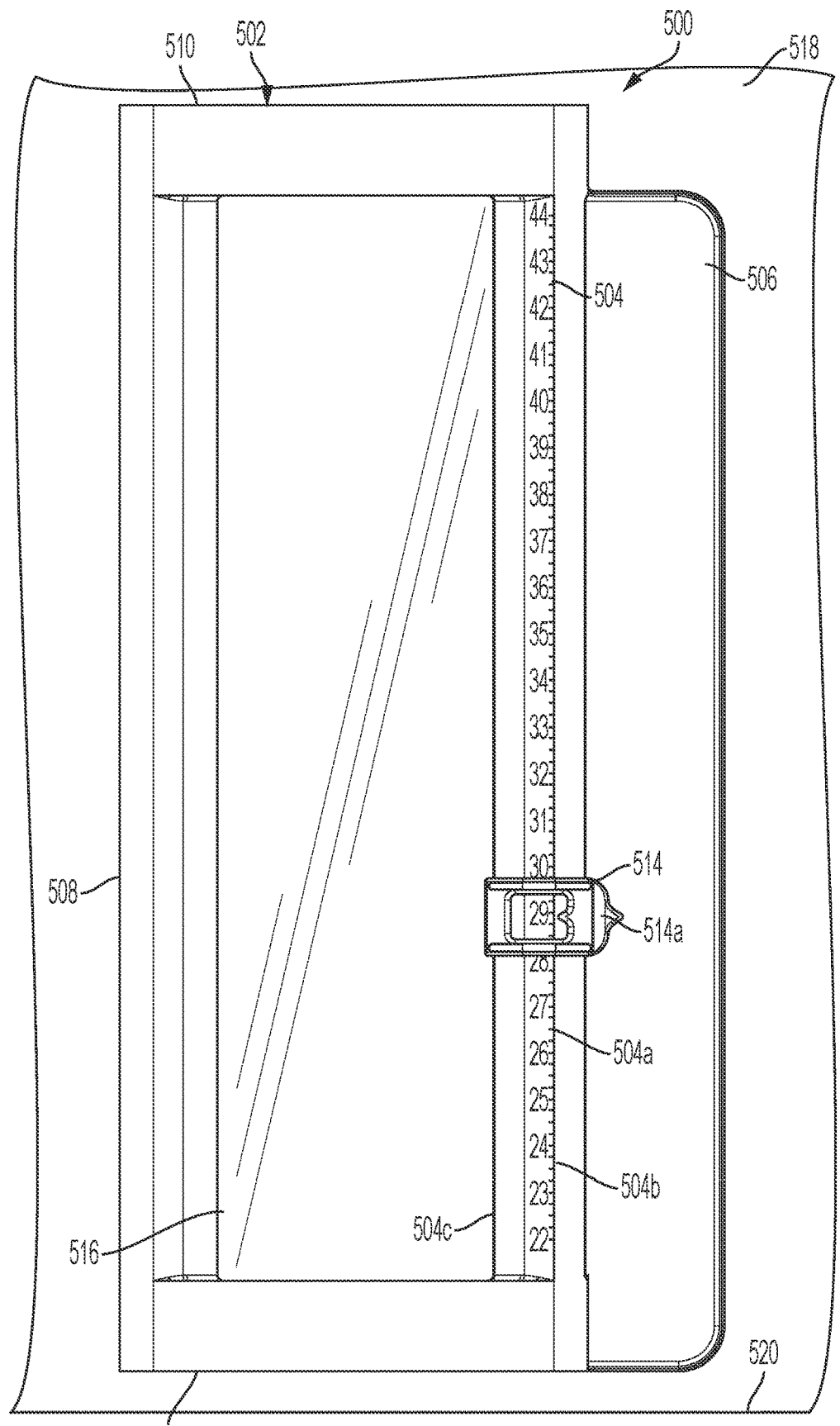

FIG. 14 is a front elevational view of the preferred embodiment of the invention, mounted on a wall, disclosed herein.

Figure 15:
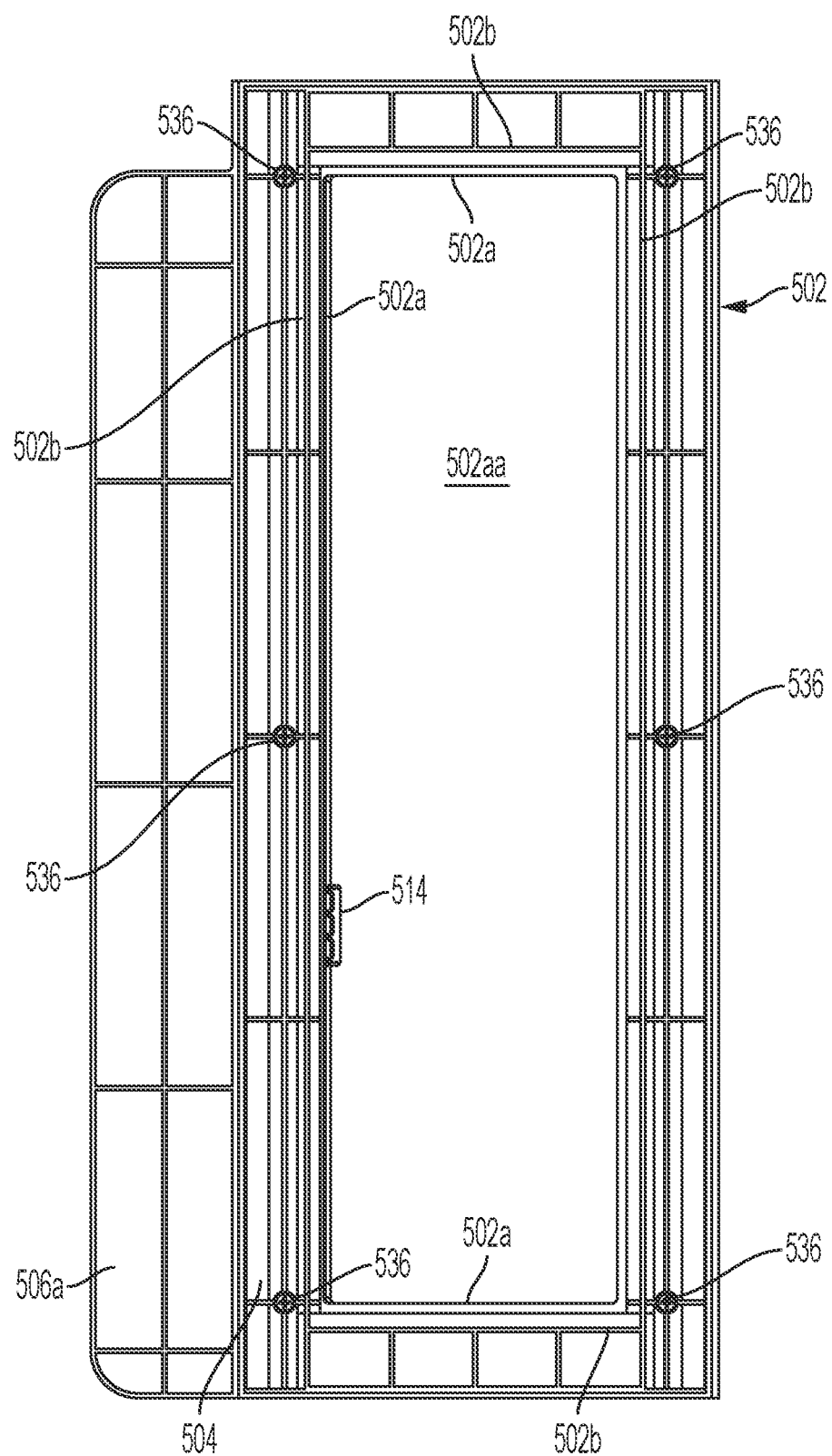

FIG. 15 is a back elevational view of the backside of the front molded panel of the preferred embodiment of the invention, without the mirror.

Figure 16:
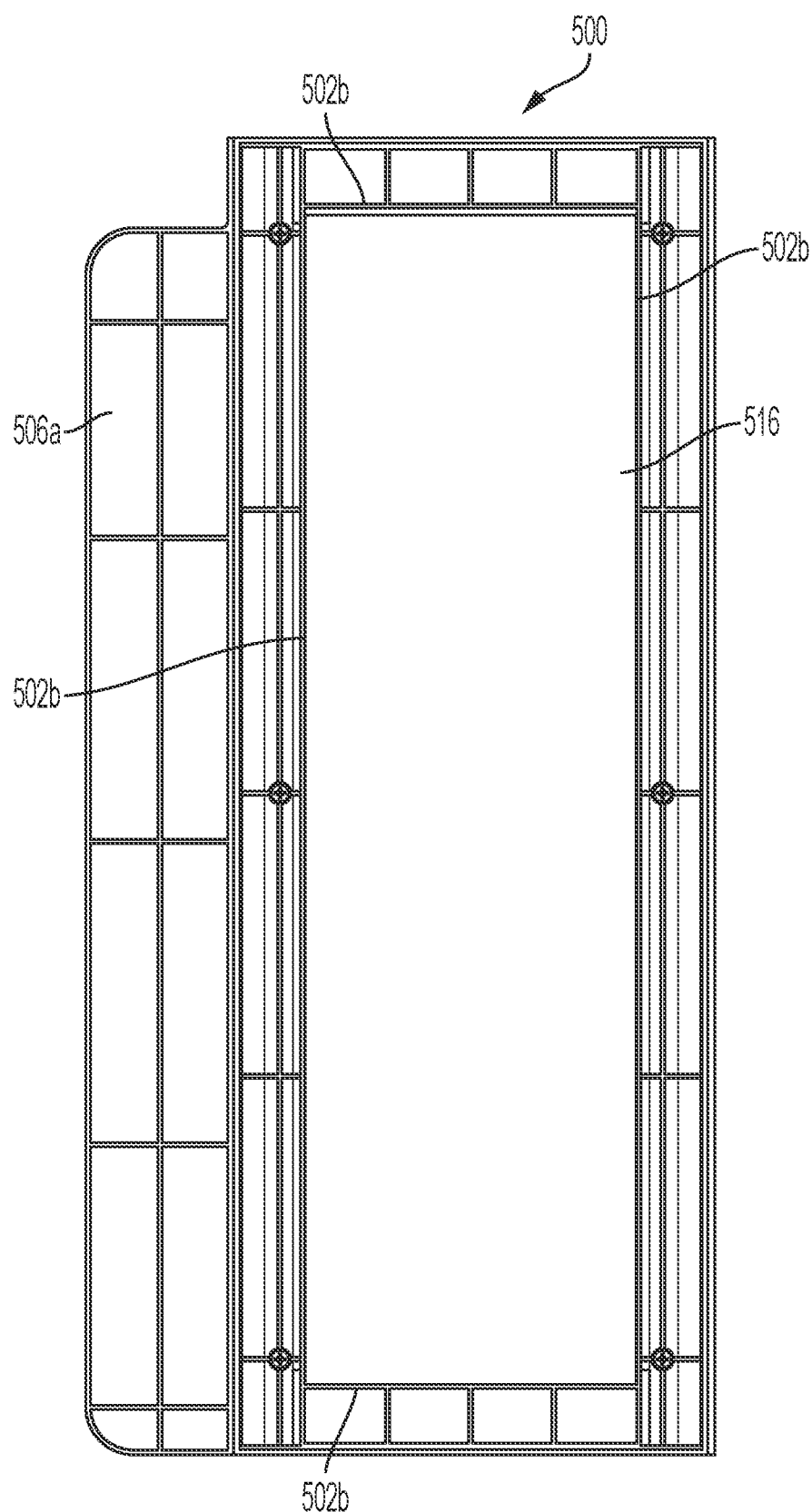

FIG. 16 is a back elevation view of the back side of the front molded panel of the preferred embodiment of the invention, with mirror positioned therein.

Figure 17A:
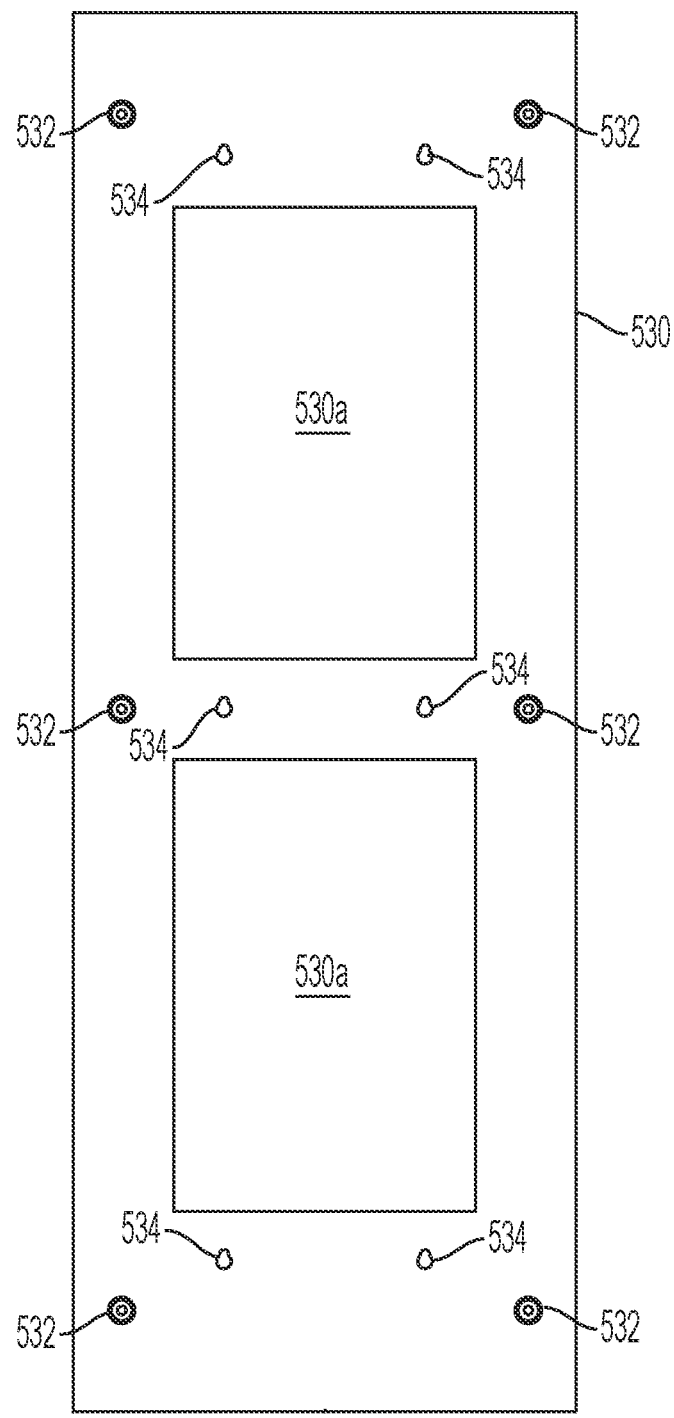

FIG. 17A is a back elevational view of the back molded panel that attaches to the front molded panel of the preferred embodiment of the invention.

Figure 17B:
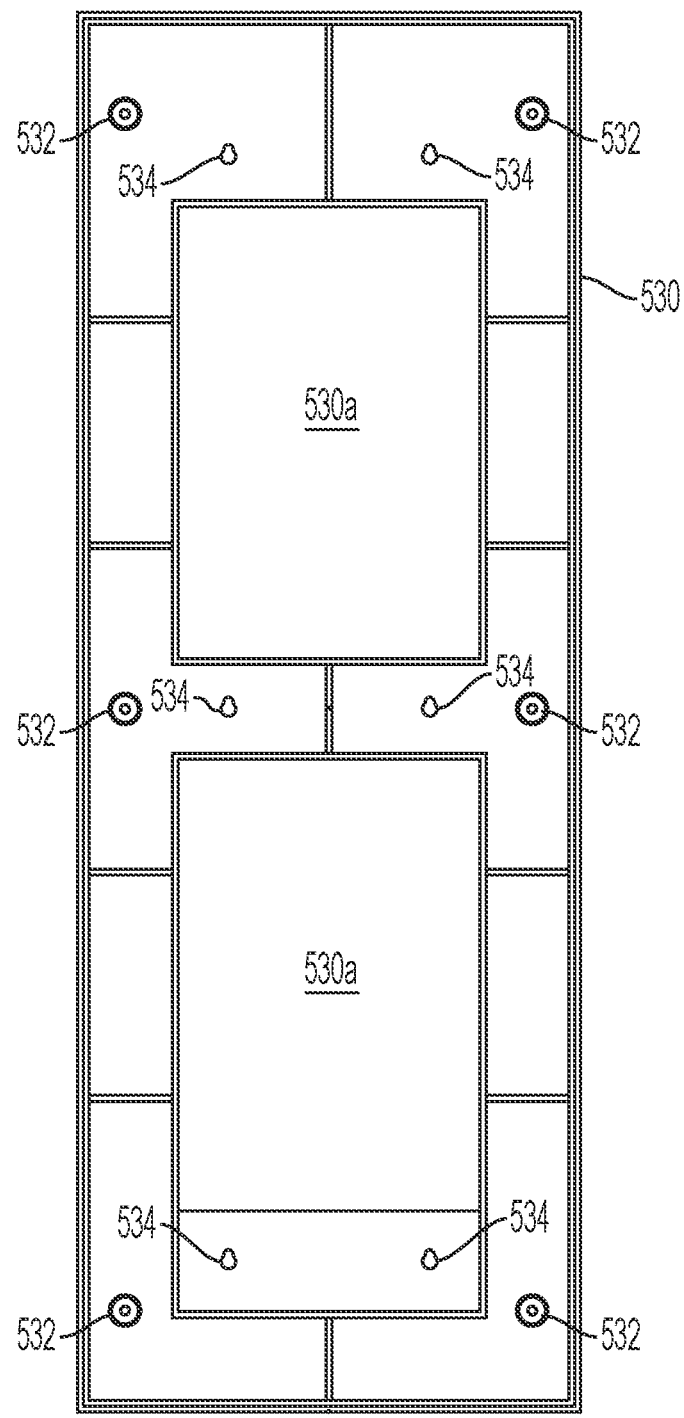

FIG. 17B is an elevational view of the front side of the invention back panel that attaches to the front panel of the preferred embodiment of the invention.

Figure 18:
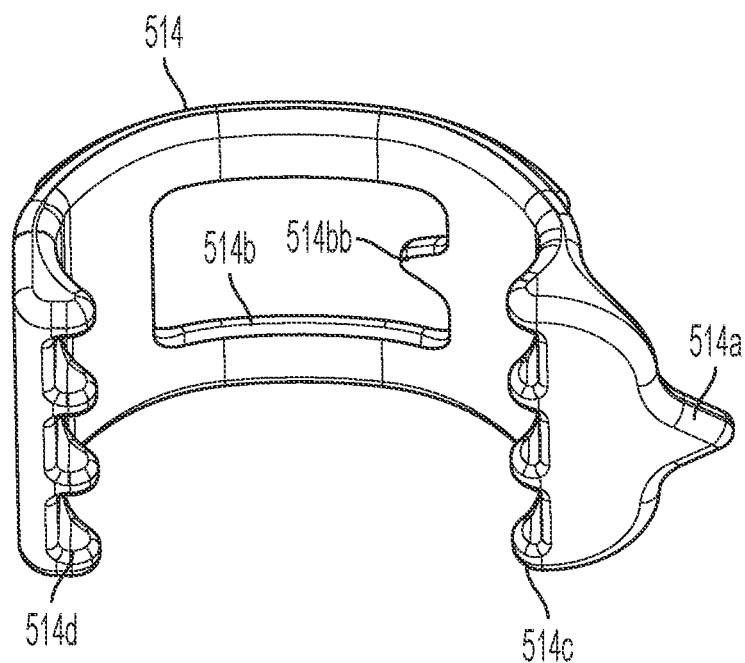

FIG. 18 is an upper perspective view of the measurement carriage of the preferred embodiment of the invention.

Figure 19:
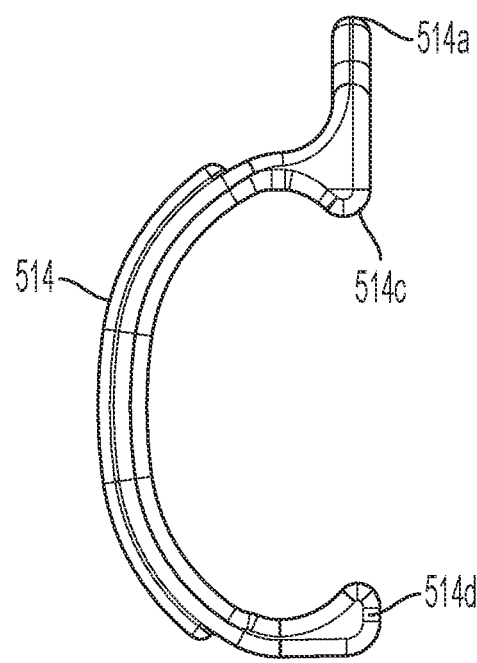

FIG. 19 is a side elevation view of the measurement carriage of the preferred embodiment of the invention.

Figure 20:
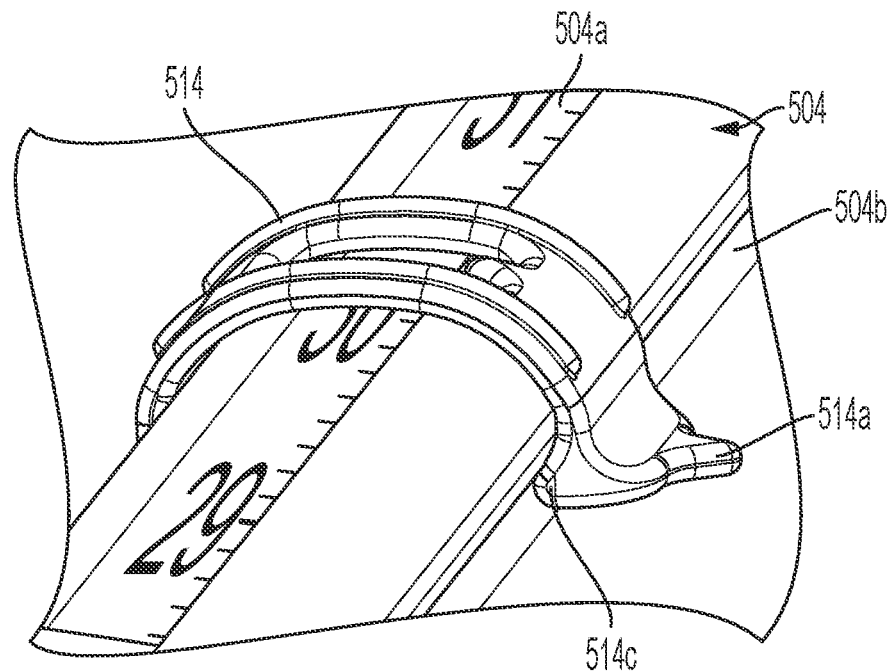

FIG. 20 is a cutaway view of the measurement carriage and small section of the vertical track slot right side in accordance with the preferred embodiment of the invention disclosed.

Figure 21:
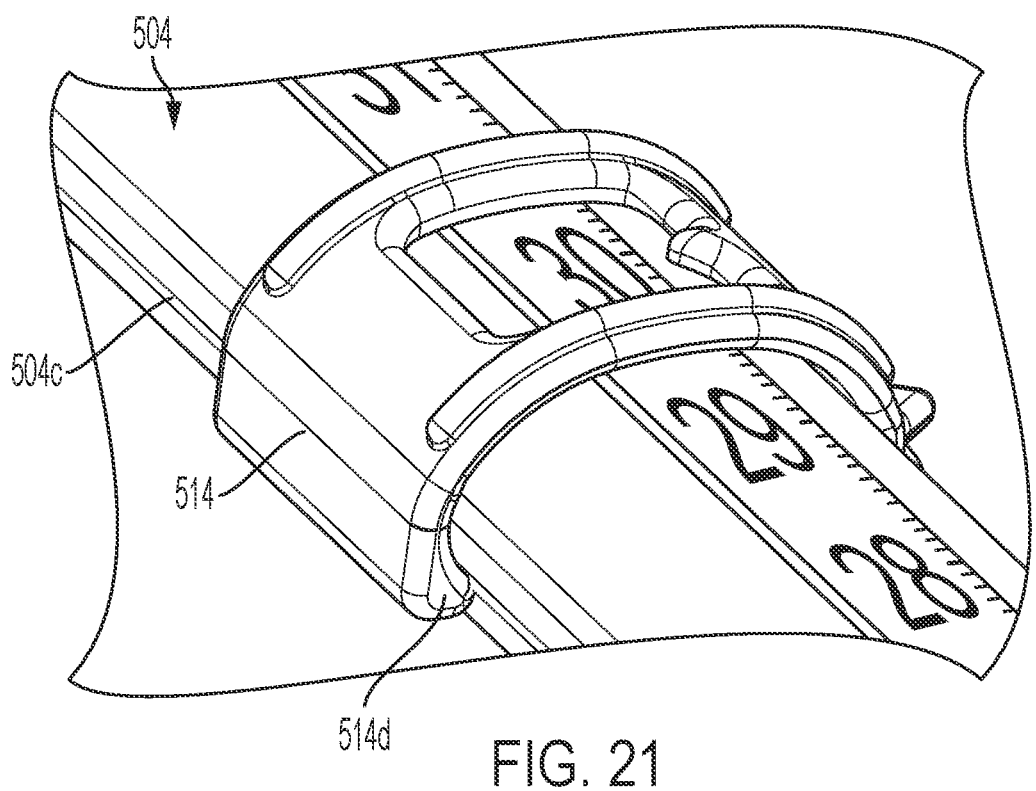

FIG. 21 is a cutaway view of the measurement carriage and a small section of the vertical truck and slot left side in accordance with the preferred embodiment of the invention disclosed.

Figure 22:
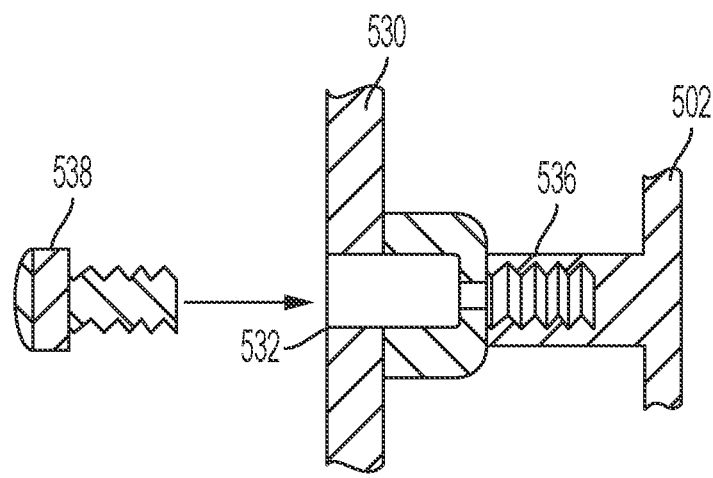

FIG. 22 is a cut-a-way in cross-section elevation segment of the back panel aperture for receiving a wall mounting fastener bolt or screw head in the preferred embodiment of the invention.

Figure 23:
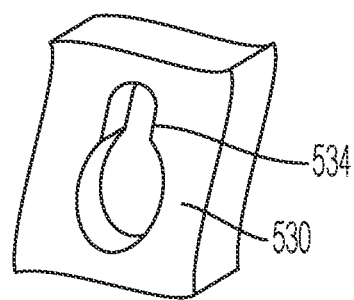

FIG. 23 is a perspective cross-sectional view of a screw recess in the back panel; and set well threaded fastener protrusion in the backside of said front panel in the preferred embodiment of the invention.

DETAILED DESCRIPTION OF THE INVENTION

Preferred Embodiment of the Invention; FIGS. 14-23

Referring now to FIG. 14, the preferred embodiment of the invention, is shown as child height measuring device 500, mounted on a wall surface 518, above a floor surface 520.

The child height measuring device 500 is comprised of a front panel 502, molded as a single piece of plastic, a flat, back or rear panel 530 (FIGS. 17A and 17B) (not shown in FIG. 14), and a central rectangular mirror 516. The flat, back molded panel 530 (FIGS. 17A and 17B) is attached (not shown) to the front molded panel by a plurality of screw fasteners, that also hold the mirror 516 in place.

In FIG. 14, the child height measuring device 500 includes a rectangular, front panel 502, plastic-molded, that includes a integrally-molded semi-circular shaped, vertical track 504 that includes indicia, displaying a distance measuring scale 504a, having a plurality of vertical numbers used to determine a child's height, when a child is standing in front of the mirror 516, which can be either in inches or centimeters, vertically displayed on vertical track 504. A measuring carriage 514 is movably mounted for manual movement along vertical track 504. The carriage 514 includes an external pointer 514a that points horizontally in the direction of a flat, lower (in the plane of the mirror 516), panel 506, extending on the right, horizontally right, that can receive child height bearing indicia, written by a user with a marker, manually on the surface of the extending panel 506 and its vertical length to the right of carriage 514 and vertical column 504.

The child height measuring device 500, mounted on a wall 518, includes a rectangular, center-mounted mirror 516, that a child or minor, will be positioned to stand in front of, during measurement, by an adult or self-measurement by a minor. Except for mirror 516, that fills in a large rectangular open passage 502aa, through front panel 502, and carriage 514, the front panel 502 of device 500 is a single, molded panel that includes a semi-cylindrical vertical track 504, a flat, lower, extending right, rectangular panel 506, a vertical frame member 508 on the left side of mirror 516, a central large open rectangle 502aa, (FIG. 15) and top and bottom frame members 510 and 512.

The child height measuring device 500 has a front single piece, molded plastic panel 502, FIG. 14, and also has a flat, back panel 530, also a single piece of molded plastic, shown in FIGS. 17A and 17B, (not shown in FIG. 14, 15, or 16), in operation, that is firmly secured by screws (FIG. 22), onto the backside of front panel 502, FIG. 15, shown without mirror 516, and FIG. 16, shown with mirror 516.

FIG. 15, without mirror 516, the backside of front panel 502 of child height measuring device 500 shows a rectangular slot 502aa (the exact size of mirror 516) created by two parallel walls 502a and 502b, of different in heights, that form and define open rectangular space 502aa, that receives the mirror 516 body (not shown in FIG. 15) formed on the backside of front panel 502. Once the mirror 516 is in place, as shown in FIG. 16 in the rectangular frame formed by walls 502a and 502b, the outer wall 502b being higher than wall 502a by the thickness of the mirror 516 in place, the outer wall 502b is visible in FIG. 16 surrounding mirror 516. Once the mirror is in place as shown in FIG. 16, the flat, back panel 530 of device 500, not shown in FIGS. 14, 15, and 16, is attached by screws (FIG. 22) to the device 500 front panel 502, backside to hold the back panel 530 and mirror 516 in place.

Referring to FIG. 17A, the backside of back panel 530 is shown, along with two rectangular open spaces 530a which expose the back of mirror 516, when the back panel 530 is secured to the front panel 502. The backside of the back panel 530 also has six conical recesses 532 that are sized in-depth and diameter to receive screw fasteners that include screw heads that are positioned through the screw hole recess bottom apertures when the back panel 530 and the front panel 502 are screwed together. The backside of back panel 530 also has six tear-shaped apertures 534 that are used to receive wall mounting bolts or screws, so that the entire child height measuring device 500 can be firmly hung on a wall. Each tear-shaped wall mounting aperture 534 (FIG. 23) has a smaller circular diameter along the top and a larger circular diameter along the bottom to receive the circular head of a wall fastener in the larger diameter opening that can be supported by a wall fastener smaller diameter portion along the smaller top diameter aperture.

FIG. 17B shows the front side of back panel 530, also disclosing two rectangular open spaces 530a. The screw recesses 532 of conical projections (FIG. 22 with a top hole that allows the threaded portion of the screw to pass through for attachment to screw into screw set wells 536, FIG. 15 and FIG. 16, in the backside of front panel 502, for securing the back panel 530 to the front panel 502 of the child measuring height device 500.

In FIGS. 18 and 19, the manually movable, child height measuring carriage 514 is shown, slightly larger diametrically in a semi-circular shape than the semi-circular vertical track 504 exterior surface. The body carriage 514 includes an open window 514b that has a pointed indicator inwardly 514bb that allows a user to move carriage 514 vertically and view the measuring scale 504a (in inches or millimeters) visible in the carriage window 514b with a specific child height measurement scale value near the carriage pointer window 514 to allow the user to determine the proper child height numerical value from the scale. At one free end of the carriage 514 is a very large pointer 514a, that points away from the carriage 514, and is used to point at the marking surface on flat panel 506 on the right-hand side of the front side of the front panel 502 to allow a line or other indicia to be drawn on the flat panel 506 with a marker, indicating a line showing the height of the child.

The carriage 514 has four bulbous-shaped panel connecting fasteners 514c and 514d at each free end that fit within and that slide along the vertical track 504 circular slots 504b and 504c, FIGS. 20 and 21, at the base of vertical track 504, FIG. 14, with sufficient light friction to allow manual movement of the carriage 514 vertically, but when the carriage 514 is not touched manually, allows the carriage 514 to stay in place on the vertical track 504, held in place by friction. The specific operational steps for the structural embodiment of the carriage 514 movable in the vertical track 504 arrangement are described below.

The carriage 514 is constructed of a single piece of molded plastic.

The child height measuring device 500 back panel 530 is attached to the device 500 front panel 502 by screws, once the mirror 516 has been mounted on the back side of the front panel 502. FIG. 17A shows the back side of back panel 530, with its rectangular open spaces 530a. The back panel 530 includes six recessed cylindrical slots 532 (see FIG. 22) distributed near the top, middle, and bottom of back panel 530, so that the back panel 530 can be firmly attached to the front panel 502 (not shown in FIG. 17A) by placing a threaded screw into each circular recessed slot 532. There are six spaced-apart screw receiving threaded wells 536 (FIG. 22) in the backside of front panel 502 discussed below that receive the attaching screws 538 (FIG. 22) positioned through the back panel 530 recessed slots 532.

For mounting the child height measuring device 500 on a wall, there are six wall fastener receiving apertures 534 (see FIG. 23) distributed near the top, middle, and bottom of the flat back panel 530. The apertures 534 are teardrop-shaped, with a larger diameter near the bottom of the aperture 534 and a smaller curve in diameter near the bottom of the aperture 534. The wall mounting apertures 534 are sized to receive bolt or screw head fasteners protruding from a wall surface outwardly with circular heads that can fit into the lower circular portion and then slide by gravity into the smaller diameter upper portion for firmly holding the back panel 530 to a wall surface as shown in FIG. 14. It should be noted that the distances of where the wall mounting fasteners above a floor and the distance of the child height measuring device 500 above a floor must agree with the measuring height scale 504a measurement so that the child's height will be correctly measured when the child is standing on the floor in front of the mirror on the device 500.

In operation, an adult or child supervisor would position the child standing in front of the mirror so that the child looking at the mirror will allow the child to be interested in remaining in position while the child's height is measured. The adult would then be able to determine the top level of the child's head and position carriage 514 at that specific distance which can then be recorded using a pen or marker on panel 506 next to carriage 514 where a line is drawn showing the child's height other information can be also provided the child height line positioned on panel 506.

Some of the great advantages of the preferred embodiment of the invention are efficiency and economy of construction by having a single molded front panel and a single flat molded back panel which are manually fastened by together by screws and hold a central mirror in position, without extreme complexity and construction. Also the molded height scale measuring movable carriage fits conveniently along the vertical track with sufficient radial pressure for friction, while at the same time, the carriage allows manual movement vertically of the carriage 514 along the vertical track to reach the proper child height, when measuring the child. But there is sufficient friction between the carriage 514 and vertical track 504 that the carriage 514 will remain in a stable position until manually moved to the proper height along the measuring scale.

Prior Alternate Embodiments of the Invention
Shown in FIGS. 1-13

An apparatus 100 built in accordance with a first embodiment of the invention for measuring a height of a child will first be discussed with reference being made to FIG. 1, a front elevation of the apparatus 100, which includes a track member 102, a frame member 104, disposed laterally from the track member 102 in the direction of arrow 106 to hold a mirror 108, an upper cap 108, a lower cap 110, and a carriage 112, movable upward, in the direction of arrow 114, and downward, opposite the direction of arrow 114, along the track member 102. The track member 102 includes a visible scale 116, while the carriage 112 includes an indicator 118 pointing to a location on the visible scale 116 describing a distance 120 between a surface 122 of a floor 124 extending outward from a wall 126 to which the apparatus 100 is attached and a measurement surface 128 of the carriage 112, and with the distance 120 being described, for example, in inches or centimeters. Preferably, the apparatus 100 is fastened to the wall 26 by a number of screws 130 extending through slots (not shown) in the upper cap 108 and the lower cap 110.

Figure 2:
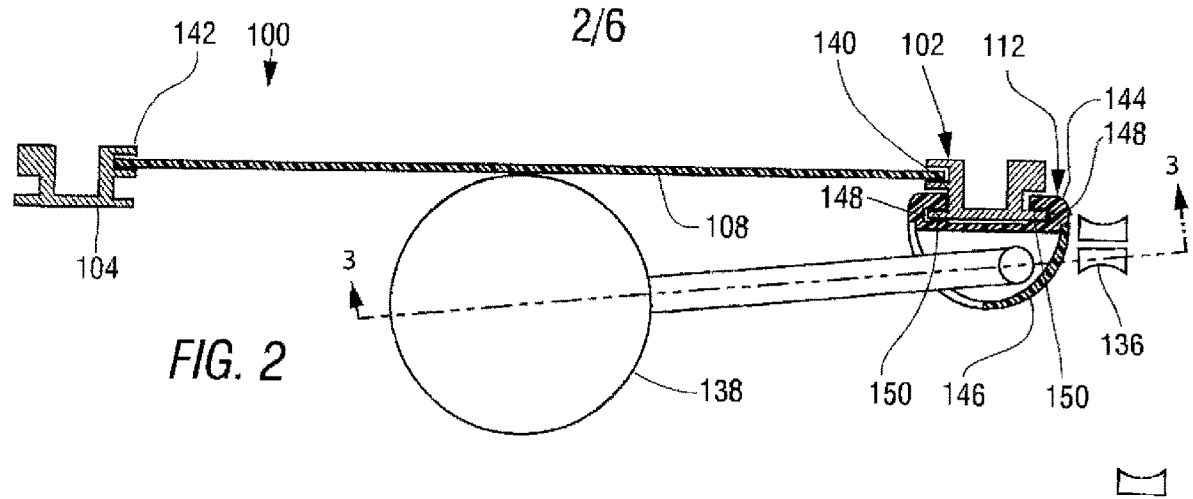
FIG. 2 is a fragmentary cross-sectional plan view of the apparatus of FIG. 1, taken as indicated by section line 2-2 therein.

FIG. 2 is a fragmentary cross-sectional plan view of the apparatus 100, taken as indicated by section line 2-2 in FIG. 1, showing the mirror 108 as being held to extend between a first slot 140 in the track member 102 and a second slot 142 in the frame member 104. The carriage 112 is shown as including a housing 144 and a cover 146. The housing 144 slides upward and downward on the track member 102, with a guiding rib 148 extending outward from each side of the track member 102 sliding within a guiding slot 150 of the housing 144.

Figure 3:
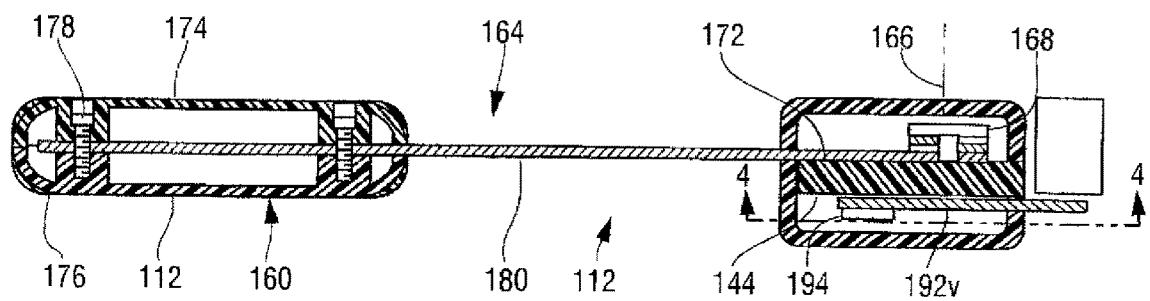
FIG. 3 is a fragmentary cross-sectional oblique elevation of the apparatus of FIG. 1, taken as indicated by section line 3-3 in FIG. 2.

FIG. 3 is a fragmentary cross-sectional oblique elevation of the apparatus 100, taken as indicated by section line 3-3 in FIG. 2, showing the measurement surface 128 of the carriage 112 as being formed along a lowest surface of a measurement structure 160 at an end 162 of a measurement arm 164, which is attached to pivot about a vertical axis 166 of the housing 144. For example, the vertical axis 166 is established by a pivot screw 168 fastened to the housing 144, with a wave washer 170 holding the measurement arm 164 against an upwardly facing surface 172 of the housing 144, while the measurement structure 160 is formed by clamping an upper section 174 to a lower section 176, with a bar 180 extending through a slot 182 within the cover 146 from the pivot screw 168 being clamped between the sections 174, 176.

Figure 4:
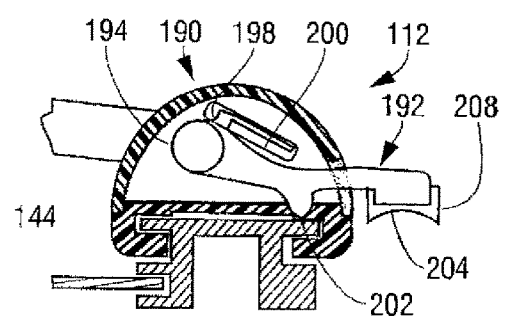
FIG. 4 is a fragmentary cross-sectional underneath plan view of the apparatus of FIG. 1, taken as indicated by section line 4-4 in FIG. 3.

FIG. 4 is a fragmentary cross-sectional underneath plan view of the apparatus 100, taken as indicated by section line 4-4 in FIG. 3, showing a braking mechanism 190 that is provided for holding the carriage 112 in place on the track member 102. The braking mechanism 190 includes a brake lever 192, which is pivotably attached to the housing 144 by a pivot screw 194. The brake lever 192 includes a spring member 196, which extends upward into a cavity 198 within the housing 144, contacting a surface 200 of the cavity 198 to provide a force holding a braking surface 202 against the track member 102. The brake lever 192 further includes a tab 204, extending within a release pad 208 to attach the release pad 208 to the brake lever 192, which is then released from contact with the track member 102 by movement of the release pad 208 in the forward direction of arrow 210. The housing 144 preferably includes a guiding pad 212 disposed adjacent to, but spaced away from, the release pad 208, so that these pads 208. 212 can be squeezed together, using outward-facing, concave surfaces 214 thereof, to release the braking mechanism 190 and to move the carriage 112 as desired.

Figure 5:
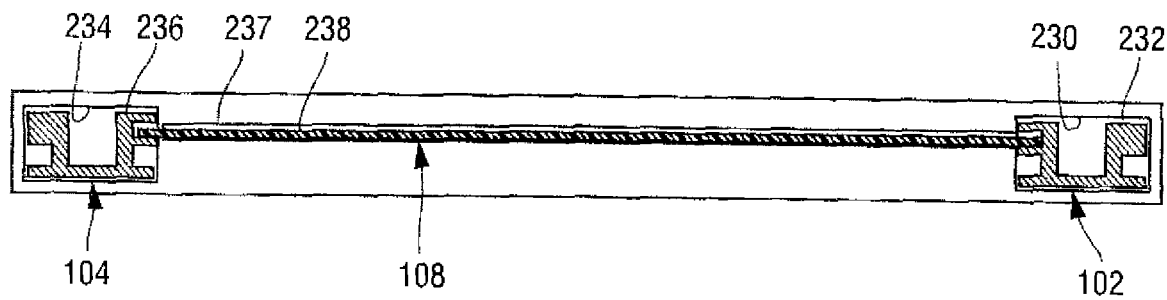
FIG. 5 is a cross-sectional plan view of the apparatus of FIG. 1, taken as indicated by section line 5-5 therein.

FIG. 5 is a cross-sectional plan view of the apparatus 100, taken as indicated by section line 5-5 in FIG. 1, showing that a lower cap 110 therein includes a first socket 230, holding a lower end 232 of the track member 102, a second socket 233, holding a lower end 234 of the frame member 104, and a central slot 236, holding a lower edge portion 238 of the mirror 108. As shown in FIG. 1, the upper cap 108 is preferably identical to the lower cap 110, with the upper cap 108 being installed in an inverted orientation to hold an upper end 240 of the track member 102, an upper end 242 of the frame member 104, and an upper edge portion 246 of the mirror 108. Both the upper cap 108 and the lower cap 110 include a number of outwardly-open sockets 238, through which screws 130 extend to attach the caps 108, 110 to the wall 126.

Figure 6:
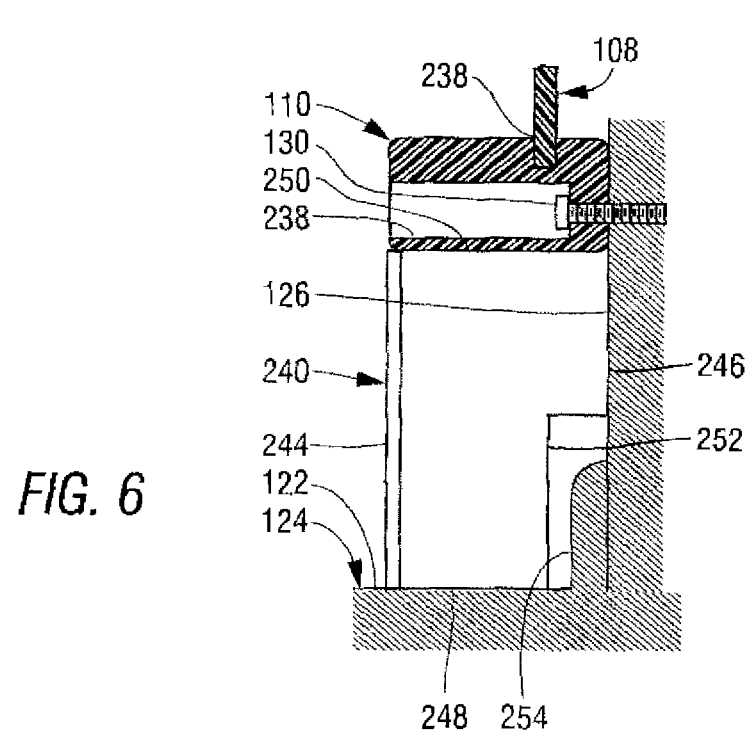
FIG. 6 is a right elevation of a lower cap within the apparatus of FIG. 1, shown as installed using an assembly fixture.

FIG. 6 is a right elevation of the lower cap 110, shown as installed on the wall 126 in first step of a preferred process for assembling and installing the apparatus 100, with this first step attaching lower cap 110 to the wall 126 with a number of screws 130 as the lower end cap 110 is held atop an assembly fixture 240, which is preferably provided with the apparatus 100 so that, during subsequent use of the apparatus 100, conditions described above in reference to FIGS. 1 and 3 will be met, with the distance 120 between the measurement surface 128 of the carriage 112 and a surface 122 8f the floor 124 being indicated by the location of the indicator 110 on the visible scale 116 as the carriage 112 is moved upward and downward along the track member 102.

For example, the assembly fixture 240 includes a pair of identical side plates 242 extending at each end of a connecting plate 244, with each of the side plates 242 including a first surface 246 configured to rest against the wall 126, a second surface 248 configured to rest against the surface 122 of the floor 124, and a third surface 250, configured to support the lower cap 110. A fourth surface 252 is recessed to avoid contact with a molding 254, which may be present.

After the first step of the assembly and installation process is completed, as described above in reference to FIG. 6, the lower end 232 of the track member 102 and the lower end 234 of the frame member 104 are inserted into the sockets 230, 233, and the lower edge portion 238 of the mirror is inserted into central slot 236, so that the track member 102, the frame member 104, and the mirror 108 extend upward from the lower cap 110. The carriage 112 may have been previously installed to slide along the track member 102, or it may be instead installed on the track member 102 at this time. In either case, the upper cap 108 is then attached to the wall 126 as shown in FIG. 1 to hold upper end portions of the track member 102, the frame member 104, and the mirror 108.

An apparatus 270 built in accordance with a second embodiment of the invention will now be discussed, with reference being made to FIGS. 7-9. FIG. 7 is a front elevation of the apparatus 270, while FIG. 8 is a cross-sectional plan view thereof, taken as indicated by section line 8-8 in FIG. 7, and while FIG. 9 is a fragmentary cross-sectional elevation thereof, taken as indicated by section line 9-9 in FIG. 8. With elements similar or identical to the elements described above in reference to the apparatus 100 being accorded like reference numerals, it is noted that the apparatus 270 includes a main plate 272, which is attached to wall 126 by a number of screws 130, an upper end cap 274, attached to the main plate 272 by two attachment screws 276, a lower end cap 278, also attached to the main plate 272 by two attachment screws 276, a track member 280, adhesively attached to the main plate 272, a visible scale 116, extending along the track member 280, and a carriage 112, engaging the outstanding ribs 148 of the track member 280 as described above regarding the first apparatus 100 so that the carriage 112 can be moved upward and downward along the track member 280 and held at a desired location, with an indicator 118 on the carriage 112 pointing to a location on the visible scale 116 describing a distance 120 between a measurement surface 128 on the carriage 112 and a surface 122 of a floor 124 extending outward from the wall 126, again as described above regarding the apparatus 100. The main plate 272 includes a curved edge section 282 extending along a right edge 284 and a left edge 285, with each of the curved sections including a outwardly curved section 286 and an inwardly curved section 288, and an open slot 290, facing in the inward direction of arrow 291 to hold a mirror 292 extending between the two curved edge sections 282.

Since the apparatus 270 is configured so that the screws 130 attaching the main plate 270 to the wall 120 are hidden by the mirror 292, the main plate 270 must be attached to the wall 120 before the mirror 292 is installed within the main plate 272. Preferably, such an attachment to the wall is done using an assembly fixture to establish a desired distance between the surface 122 of the floor 124 and a feature of the main plate 272, in the manner generally described above in reference to FIG. 6. Then, the lower end cap 278 is attached to the main plate 272 by two attachment screws 276, closing an opening at a lower end 294 of the main plate 272. Next, the mirror 292 is inserted into an opening at the upper end 296 of the main plate 272 and lowered until a lower end 298 of the mirror 292 extends into a slot 300 within the lower end cap 278. Then, the upper end cap 274 is installed to extend along the upper edge 302

As shown in FIGS. 7 and 9, the upper end cap 274 is attached to the main plate 272 by two attachment screws 276, each extending through a clearance hole 304 within the upper end cap 274 to engage a threaded hole 306 within an attachment block 308, disposed in an attachment slot 310, which is open to the adjacent left side 282 or right side 284 so that the attachment block can be inserted into the attachment slot 310. The attachment block 308 includes a distal flange 312 engaging a proximal flange 314 within the attachment slot 310. Similarly, the lower end cap 278 is attached to the main plate 272 by two attachment screws 276, each extending through a clearance hole 304 within the upper end cap 274 to engage a threaded hole 306 within an attachment block 308, disposed in an attachment slot 310, which is open to the adjacent left side 282 or right side 284 so that the attachment block can be inserted into the attachment slot 310. Again, the attachment block 308 includes a distal flange 312 engaging a proximal flange 314 within the attachment slot 310. As shown in FIG. 7, for example, a lower surface 312 of the upper end cap 274 includes a slot 314 for receiving an upper edge 316 of the of the mirror 292, while n upper surface 318 of the lower end cap 278 include a slot 320 for engaging a lower end 322 of the mirror 292.

Figure 11:
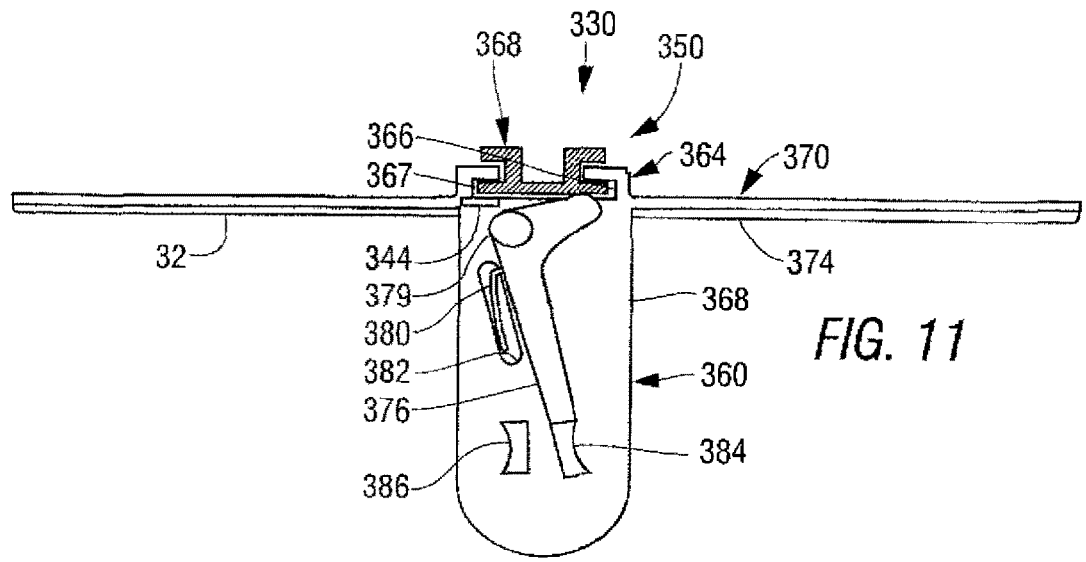
FIG. 11 is a cross-sectional plan view of the apparatus of FIG. 10, taken as indicated by section line 11-11 therein.

An apparatus 330 built in accordance with a third embodiment of invention will now be discussed, with reference being made to FIGS. 10 and 11. FIG. 10 is a front elevation of the apparatus 330, while FIG. 11 is a cross-sectional plan view thereof, taken as indicted by section lines 11-11 in FIG. 10. The apparatus 330 includes a track member 332, extending between an upper end cap 334 and a lower end cap 336, a visible scale 338 attached to the track member 332, and a carriage 340 movable upward and downward along the track member 332, The carriage 340 includes a measurement surface 342 extending along its lowest surface thereof and an indicator 344 pointing to a location on the visible scale 338 describing the distance 346 between the measurement surface 340 and a surface 342 of a floor 344 extending outward from a wall 350 to which 350 to which the apparatus 352 is attached by screws 354 extending through the end caps 334, 336. Preferably, the lower end cap 336 is installed first, being spaced away from the floor 350 by the method described above in reference to FIG. 6, through the use of an assembly fixture.

The carriage 350 further includes a housing 360 and a cover 362, which is snapped into place over the housing 360. (In FIG. 11, the housing 360 is shown with the cover 362 removed to reveal internal elements.) The housing 360 incudes a track engaging portion 364 having a pair of slots 366 sliding on a pair of ribs 367 within the track member 332, a forward extending portion 368 providing controls for moving and stopping movement of the carriage 350, and a downward extending portion 370 holding a mirror 372, which is held in place on the housing 360 by a snap-on mirror frame 374. For example, a brake lever 376 is provided for engaging a surface 378 of the track member 332 to prevent movement of the carriage 350 along the track member 332. The brake lever 376 is pivotally mounted on the forward extending portion 368 of the housing 360 by a pivot screw 379, with a spring portion 380 of the brake lever 376 engaging a cavity 382 within the forward extending portion 368 to provide a force engaging the track member 332. This force is overcome, allowing movement of the carriage 350 along the track member 332 by pushing a concave surface 384 attached to the brake lever 376. The carriage 350 is then moved into a desired position by holding the concave surface 384 and a contact surface 386 squeezed together.

Figure 12:
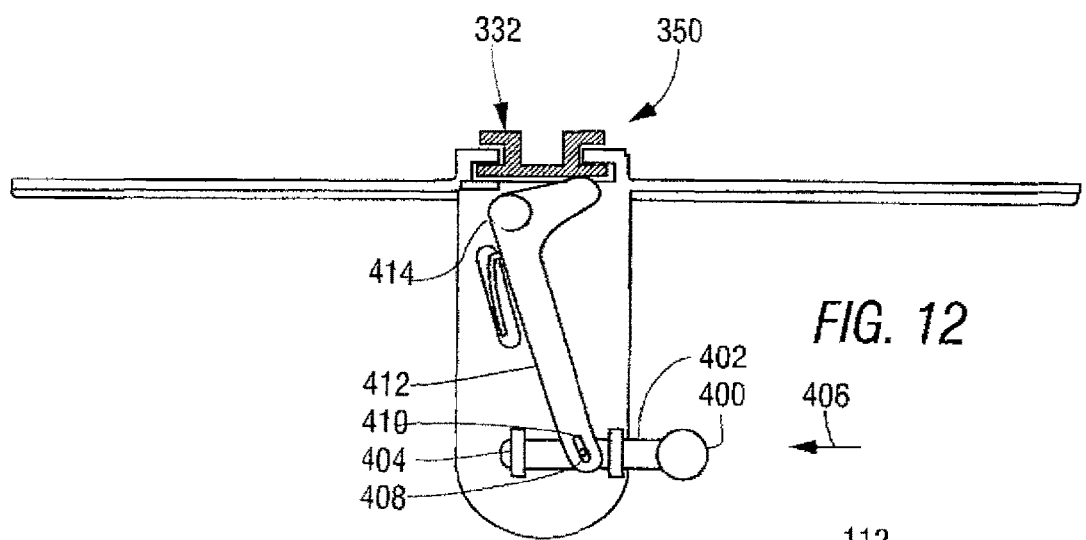
FIG. 12 is a plan view of a carriage within the apparatus of FIG. 10, shown as configured in accordance with an alternative embodiment of the invention.

An alternative embodiment for releasing and moving the carriage 350, 112 will now be discussed, with reference being made to FIGS. 12 and 13. FIG. 12 is a plan view of the carriage 350 as configured in accordance with the alternative embodiment, shown with a cover 362 removed therefrom to reveal internal elements, while FIG. 13 is a fragmentary cross-sectional underneath plan view of the carriage 112, within either the apparatus 100 or the apparatus 270, with the cross-sectional view being taken as indicated by section lines 4-4 in FIG. 3, and wherein the carriage 112 is configured in accordance with the alternative embodiment. As shown in FIG. 12, when an external knob 400, attached to a non-circular shaft 402, to slide when mounted in non-circular holes 404, is pushed in the direction of arrow 406, a pin 408, attached to the non-circular shaft 402 to extend through a slot 410 in a brake lever 412, causes the brake lever 412 to rotate about a pivot screw 414, being pulled away from the track member 332. As the brake lever 412 is then held away from the track member 332, the carriage 350 can be moved upward and downward, with the spring member 415 again holding the brake lever 412 against the track member 332 after the external knob 400 is released. Similarly, as shown in FIG. 13, when an external knob 420, attached to a non-circular shaft 22, slidably mounted in non-circular holes 424, is pulled in the direction of arrow 426, a pin 428, attached to the non-circular shaft 422 to extend through a slot 430 in a brake lever 432, causes the brake lever 432 to rotate about a pivot screw 434, being pulled way from the track member 102. As the brake lever 432 is then held away from the track member 102, the carriage 112 can be moved upward and downward, with the spring member 435 again holding the brake lever 432 against the track member 102 after the external knob 400 is released.

It is noted that the various versions and embodiments described above may be provided in kit form for installation in a house or other building.

While the invention has been described in terms of a preferred embodiment, and number of alternate embodiments with some degree of particularity, it is understood that these descriptions are given only by way of example, and that many variations, including the combination of elements of the various embodiments, may be made without departing from the spirit and scope of the invention, as defined within the appended claims.

The invention claimed is:

1. An apparatus for measuring a height of a child standing at a predetermined location, wherein the apparatus comprises:
 a housing mountable on a vertical wall, said housing having a plastic, molded, front panel for measuring the height of a child standing near a vertical wall, said front panel with a front side that includes a vertical track member and a back side, said front panel having a central open space opening,
 a mirror mounted in said front panel central open space opening;
 a molded back panel attached to said molded front panel back side, for securing said mirror against said front molded panel;
 said vertical track member formed in said front panel;
 a visible measuring scale attached to the track member; and a carriage attached to the track member to be movable along the track member only vertically, and an indicator moving adjacently along the visible scale, wherein the indicator points to a place on the visible scale describing a vertical distance between the location and the floor.

2. The apparatus of claim 1, additionally comprising:

said front panel central open space opening peripheral border that includes on the front panel back side, peripheral opening border flanges sized for receiving said mirror.

3. The apparatus of claim 1, additionally comprising:

said front panel having a flat rectangular surface, next to and parallel to said vertical track, extending horizontally for receiving indicia from a marker for indicating information regarding the height of a child during measurement of the child.

* * * * *